US011596299B2

(12) United States Patent
Mantovani et al.

(10) Patent No.: US 11,596,299 B2
(45) Date of Patent: Mar. 7, 2023

(54) SURGICAL MOUTH GAG

(71) Applicant: FONDAZIONE IRCCS "CA' GRANDA—OSPEDALE MAGGIORE POLICLINICO, Milan (IT)

(72) Inventors: Mario Mantovani, Milan (IT); Lorenzo Pignataro, Milan (IT); Vittorio Rinaldi, Rome (IT)

(73) Assignee: FONDAZIONE IRCCS "CA' GRANDA—OSPEDALE MAGGIORE POLICLINICO, Milan (IT)

( * ) Notice: Subject to any disclaimer, the term of this patent is extended or adjusted under 35 U.S.C. 154(b) by 133 days.

(21) Appl. No.: 16/759,560

(22) PCT Filed: Oct. 29, 2018

(86) PCT No.: PCT/IB2018/058428
§ 371 (c)(1),
(2) Date: Apr. 27, 2020

(87) PCT Pub. No.: WO2019/082170
PCT Pub. Date: May 2, 2019

(65) Prior Publication Data
US 2020/0288958 A1 Sep. 17, 2020

(30) Foreign Application Priority Data
Oct. 27, 2017 (IT) .................. 102017000122318

(51) Int. Cl.
A61B 1/24 (2006.01)
A61B 1/32 (2006.01)

(52) U.S. Cl.
CPC . A61B 1/24 (2013.01); A61B 1/32 (2013.01)

(58) Field of Classification Search
CPC .................. A61B 1/24; A61B 1/32
(Continued)

(56) References Cited

U.S. PATENT DOCUMENTS 2,374,863 A * 5/1945 Guttmann ............... A61B 1/32
600/224
2,476,675 A 7/1949 McIvor
(Continued)

FOREIGN PATENT DOCUMENTS

WO 2006054301 A2 5/2006

Primary Examiner — Eduardo C Robert
Assistant Examiner — Tara Rose E Carter
(74) Attorney, Agent, or Firm — Browdy and Neimark, P.L.L.C.

(57) ABSTRACT

The present invention describes an improved surgical mouth gag for the exposure of the palatal and oropharyngeal region of a patient comprising a frame (2) adapted to be arranged in use around the mouth of the patient and a tongue depressor system (21, 30) insertable in the oral cavity of the patient and movable with respect to the frame (2), the tongue depressor blade (21, 30) comprising two elements articulated to each other, able to mobilise fully in a graduated way the entire tongue base both in the caudal and posterior-anterior direction. The metal arch (2) supports and anchors the aforesaid tongue depressor system, by resting on the upper premolar and molar teeth (respecting the incisors) and acts as an anterior window adapted to guarantee both optimal exposure of the palatal structures and of the isthmus of the fauces and to facilitate palatal and oropharyngeal surgery in general and that of obstructive sleep disorders in particular.

19 Claims, 16 Drawing Sheets

(58) Field of Classification Search
USPC .................................................. 600/237–245
See application file for complete search history.

(56) References Cited

U.S. PATENT DOCUMENTS

| | | | | |
|---|---|---|---|---|
| 3,509,873 | A | * | 5/1970 | Karlin .................... A61B 17/02 600/226 |
| 4,151,837 | A | * | 5/1979 | Millard, Jr. .............. A61B 1/24 600/215 |
| 2008/0319270 | A1 | * | 12/2008 | Rosenberg ............... A61B 1/24 600/238 |
| 2016/0287224 | A1 | * | 10/2016 | Castro ................ A61B 17/0206 |

* cited by examiner

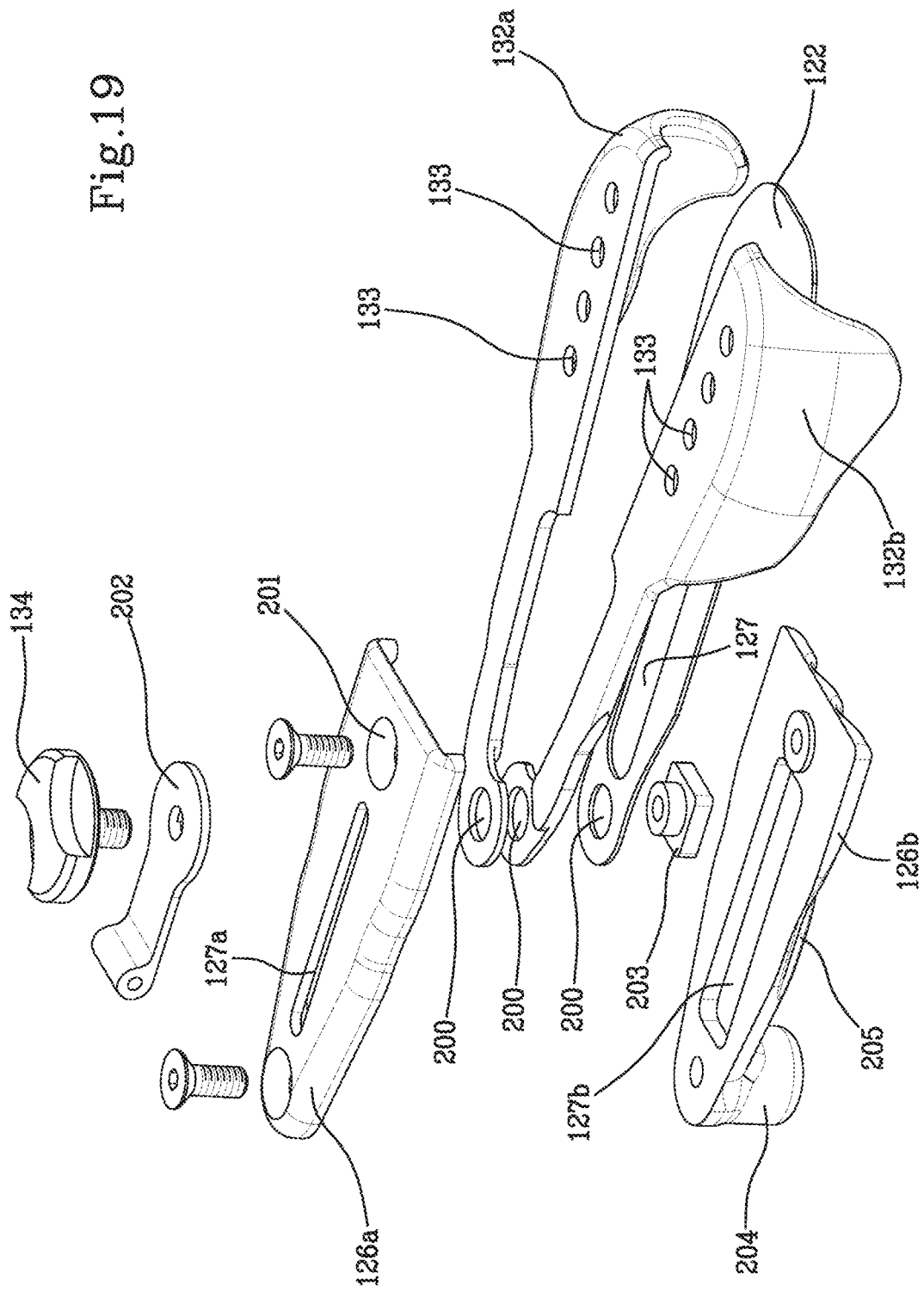

SURGICAL MOUTH GAG

TECHNICAL FIELD

The present invention relates to an improved surgical mouth gag comprising a metal arch and a tongue depressor blade able to obtain optimal exposure of the palatal structures and of the isthmus of the fauces and to facilitate the performance of palatal and oropharyngeal surgery in general and that of obstructive sleep disorders in particular.

PRIOR ART

Normally, the muscles attached to the walls of the upper airways also have the task of keeping the respiratory tracts open during inspiration so as to allow the flow of air into the lungs. When the muscles of the soft palate, of the uvula, of the lateral pharyngeal walls and of the tongue are not able to guarantee sufficient rigidity for the walls of the upper airways (of the pharyngeal tract in particular), the relaxed tissues, collapsing, can simply move closer and vibrate as air passes through, causing snoring or, in more severe cases, create complete obstruction of the upper airways and prevent the passage of air to the lungs, producing apnoea. One of the therapies for snoring and/or obstructive apnoea is surgery, both of the demolition/resection and the functional type without demolition or resection.

Recently (in 2012) a new surgical procedure was introduced without demolition or resection called "velo-uvulo-pharyngeal lift", "VUPL" or "Roman blinds technique", which leads to the suspension, shortening through muscle plication, advancement and stiffening of the soft palate and of the lateral pharyngeal walls through the use of suture threads able to anchor them to specific surrounding fibro-osseous structures, in the case in question to the posterior nasal spine, to the pterygomandibular raphe and to the pterygoid hamulus.

Such surgical procedure, initially performed with traditional, non-absorbable threads, later (in 2013) underwent a rather substantial evolution thanks to a completely innovative suture material that had never been used before in the oral and pharyngeal district: "barbed sutures", i.e. "self-locking" suture threads which, thanks to the presence of special spicules sculpted along the wall thereof, are able to act on the tissues in a rather uniform way and without needing to be knotted.

In order to be able to perform this type of surgery in a suitable way and without any difficulties, it is essential to have access to specifically designed tools in order to provide optimal exposure of the pharyngeal-palate district on which to operate.

Currently, mouth gags are used, placed between the upper jaw and the lower jaw (mandible) to keep the mouth open during the surgical procedure performed at the oropharyngeal cavity, possibly provided with a tongue depressor blade and/or other accessories.

Known mouth gags are for example the McIvor one (U.S. Pat. No. 2,476,675), the Davis-Mayer, Dingmann, Crochard or WO2006/054301 ones, provided with a tongue depressor blade anchored to a gag resting on the front teeth of the upper arch.

For example, the McIvor gag was used for over 65 years and is illustrated in FIG. 1.

A drawback of these traditional mouth gags, that make use of resting on the anterior dental elements of the upper arch, is the impossibility to have suitable exposure of the "hard palate"-"soft palate" junction, which is of utmost importance in modern surgery for snoring and obstructive apnoea of retropalatal origin.

A further drawback of known mouth gags is that they do not allow the suitable and bilateral exposure of the base of the tongue at glossotonsillar sulcus level (transition site between the lingual tonsil and palatine tonsil) as they are not able to simultaneously advance the base of the tongue fully, i.e. the median portion and both the lateral portions.

In fact, even with a tongue depressor provided with a suitable blade to fully embrace the base of the tongue (including both the amygdalo-glossal sulci) it could never be positioned at that level as it would not pass through the space that separates the lower molars of the two sides, normally with rather smaller dimensions with respect to those of the lingual base. Therefore, necessarily having to use a blade with a reduced width, compatible with the inter-molar distance, once the median part of the base of the tongue has been lowered (alone or, better, with just one of the lateral portions) it is inevitable that one or both of the lateral parts escape from the tongue depressor and rise upwards again (as can be clearly seen in FIG. 1), hence covering the underlying lateral anatomical structures, palatine tonsils, pharyngeal palatal muscles and pterygomandibular raphe in particular, obstructing surgery.

A further drawback of known mouth gags is that, by resting on the upper incisors, as well as preventing the direct viewing of the junction between the hard and soft palate, they can cause lesions to these dental elements during attempts to obtain more suitable exposure.

The object of the present invention is to provide an improved surgical mouth gag able to suitably expose the hard palate-soft palate junction and suitably and bilaterally expose the anatomical structures situated to the sides of the amygdalo-glossal sulcus.

A further object of the present invention is to allow free access to the operating area, the palate and the isthmus of the fauces, with surgical tools, thanks to the optimal exposure of the surrounding anatomical structures, safely and effectively moving apart the walls of the oral cavity acting on the tongue, the upper jaw and the lower jaw.

Another object of the present invention is to prevent the risk of harming the upper incisors.

A further object of the present invention is to prevent the formation of mono- or bilateral eversion, of the lateral portion of the lingual root, a rather annoying drawback for the surgeon but inevitable when using a traditional tongue depressor provided with a blade that has an insufficient width to cover the entire width of the lingual base itself.

Another object of the present invention is to provide an improved surgical mouth gag that can be inserted and removed safely and simply in the oral cavity.

A further object of the present invention is to have an instrument that is highly flexible to use and that adapts quickly and simply to the various shapes of patients' oral cavities.

OBJECT OF THE INVENTION

The present invention describes a surgical mouth gag for exposing the palatal and oropharyngeal region of a patient, according to the description in the appended claim 1.

Other advantageous aspects of the surgical mouth gag are included in the dependent claims from 2 to 15.

The invention confers the main technical effect of suitably exposing all the oral, palatal and pharyngeal structures subject to specific surgery (snoring and apnoea) and traditional surgery (e.g. tonsillectomy procedure, oropharyngeal surgery, etc.).

In particular, the invention, as described, achieves the technical effects of:

reducing the risk of dental lesions, in particular of the upper incisors;

optimising the exposure of the anatomical structures subjected to new surgery with barbed sutures, in order to create a tensile structure able to anchor to natural and stable anatomical grips (posterior nasal spine, pterygoid hamulus, pterygomandibular raphe) the soft tissues that form the palatal and pharyngeal tract of the upper airways so as to confer a basic rigidity thereto that is sufficient to withstand the negative internal pressure created by inspiration without collapsing when the muscles contained within their walls are not able to do so;

allowing the lingual base to advance fully to the glossotonsillar sulci using a tongue depressor blade with a suitable width not conditioned by the lower inter-molar distance (normally smaller than the width of the lingual base).

The mentioned technical effects/advantages cited and other technical effects/advantages of the invention will emerge in further detail from the description provided herein below of an example of embodiment provided by way of approximate and non-limiting example with reference to the attached drawings.

BRIEF DESCRIPTION OF THE DRAWINGS

FIG. 19 shows a partially exploded view of the tongue depressor blade.

DETAILED DESCRIPTION OF PREFERRED EMBODIMENTS OF THE INVENTION

Figure 1:
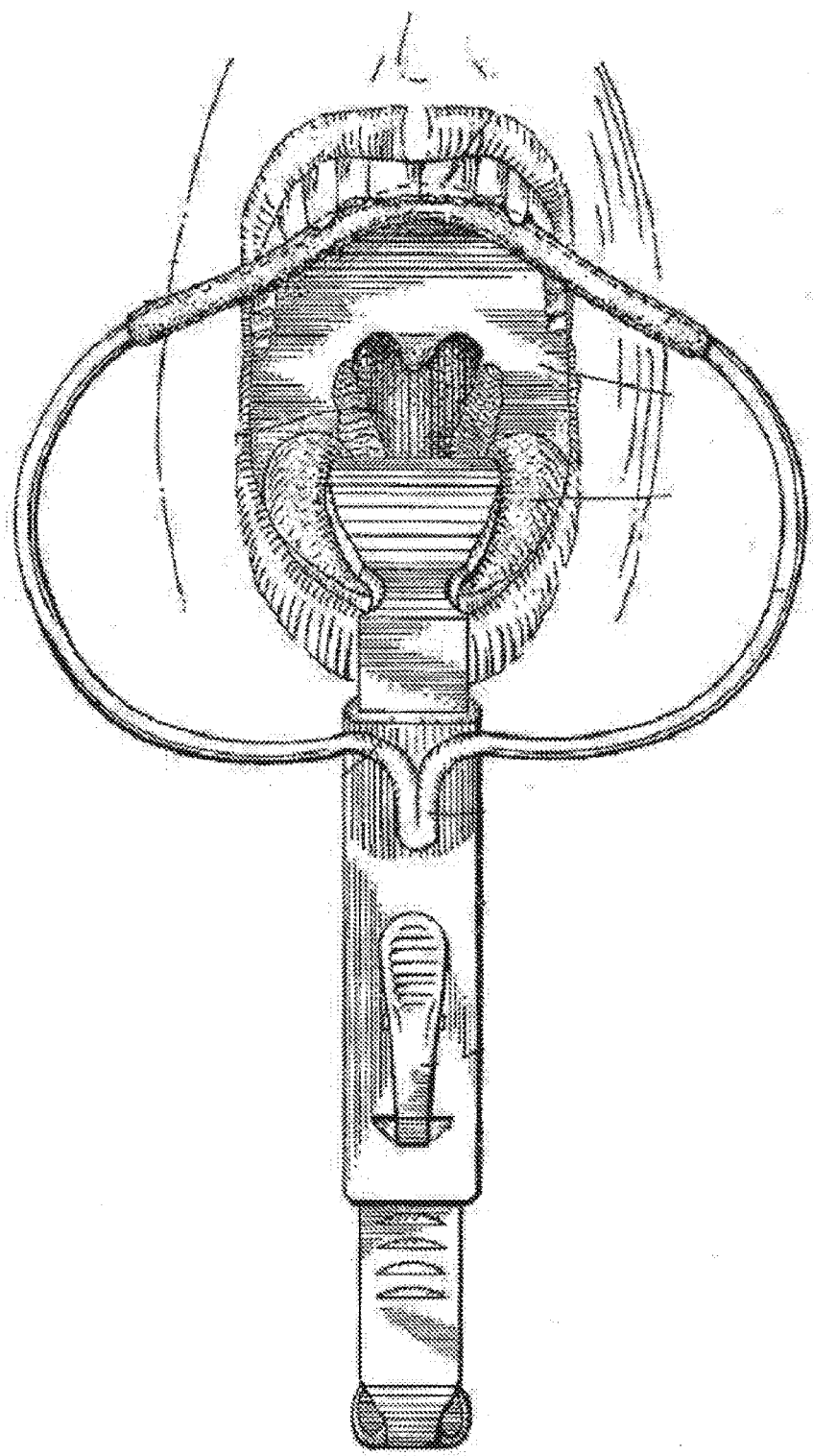
FIG. 1 shows a known surgical mouth gag.

In a first embodiment, the present invention describes a surgical mouth gag 1 for the exposure of the palatal and oropharyngeal region of a patient comprising a perioral supporting arch or frame 2 adapted to be arranged, during use, around the mouth of the patient. In particular, the frame 2 is larger than the maximum aperture of the mouth, so as to keep the mouth in that position.

As indicated below, the term "vertical" means a substantially similar, but not identical direction to the arrangement of the teeth, a vertical direction being defined in the present description as "upper" or "above", i.e. towards the upper jaw, and the opposite vertical direction being defined as "lower" or "downwards", i.e. mandibular towards the lower jaw. In other words, the vertical direction lies on the median sagittal plane (arranged in the vertical direction and passing through the interparietal suture and so as to divide the skull into two specular halves, right and left).

"Lateral" means a direction corresponding to the width of the oral cavity (distance between the lower molars on the right side and those on the left side), while a lateral direction is defined as a "buccal" direction, i.e. towards the cheeks and the opposite longitudinal direction is defined as a "lingual" direction, i.e. towards the tongue and towards the sagittal plane. The lateral direction lies on a horizontal plane parallel to the transverse plane (that separates the upper, maxillary part from the lower, mandibular, part).

The term "internal" or "towards the inside" means in the direction of the oral cavity and of the base of the tongue. "External" or "outside" means a direction away from the oral cavity.

Although these indications are defined when the frame of the mouth gag is arranged in use on the patient's face around the mouth, they can also be used to describe the configuration of the various components when the gag is removed from the oral cavity.

The frame 2 comprises a mandibular crossmember 3, at least a maxillary crossmember 5a, 5b and two uprights 4a, 4b that connect the mandibular crossmember 3 to the maxillary crossmember 5a, 5b, with a substantially rectangular shape, with the upper side partially open in a central area. Preferably, the gag 1 comprises two maxillary crossmembers 5a, 5b. The frame 2 also comprises two elements or upper arms 8a, 8b adapted to rest on the upper premolars and molars when in use, removably and movably fixed onto each maxillary crossmember 5a, 5b. In the event in which the frame 2 comprises only one maxillary crossmember, the gag will only comprise a single resting arm movably connected thereto.

Once the clamping element 12 has been released, each upper arm 8a, 8b can be extended or shortened, with respect to the frame 2, making it slide through each support element 7a, 7b.

Figure 2:
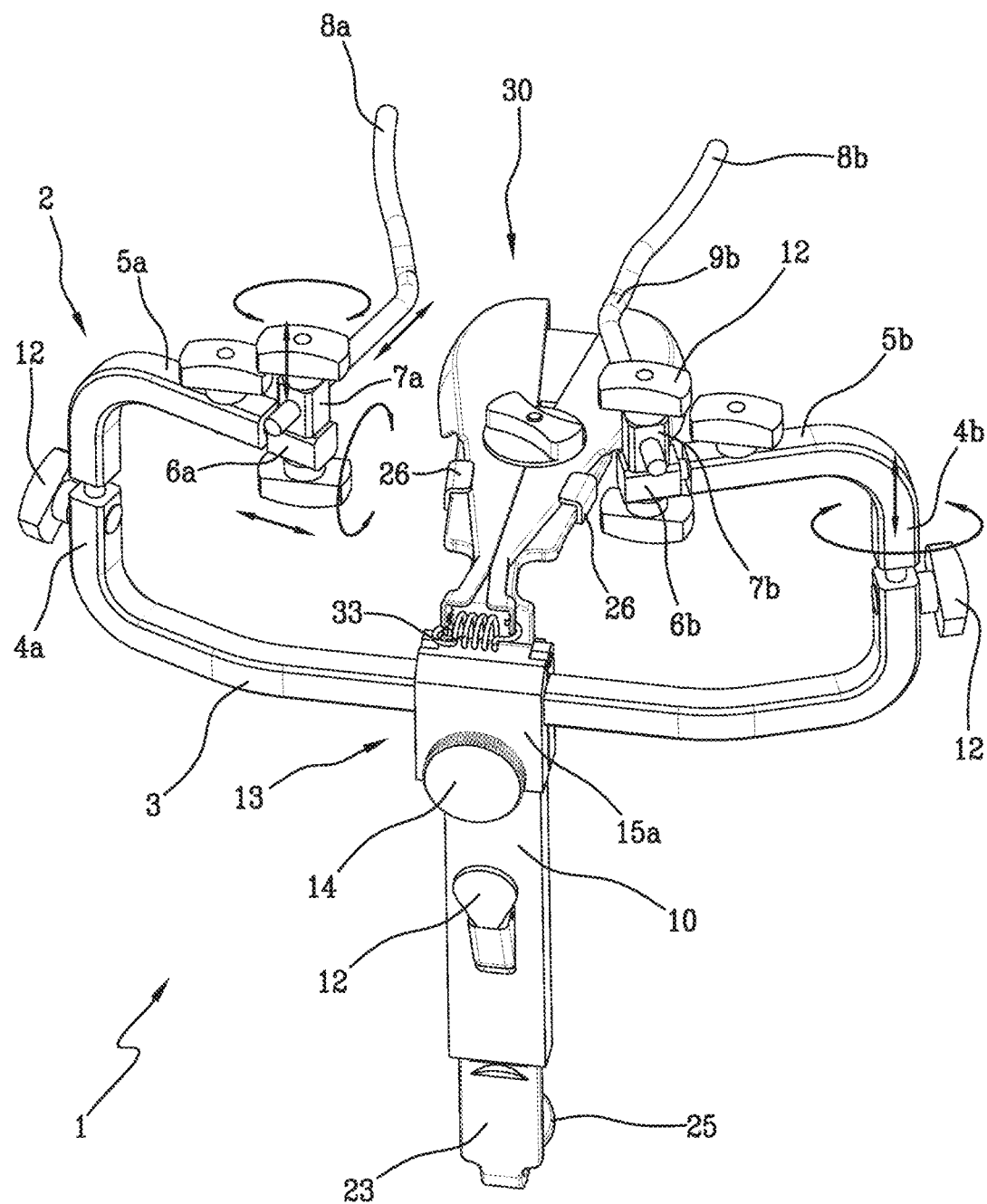
FIG. 2 shows a rear perspective view of a surgical mouth gag according to a first embodiment of the present invention.

Furthermore, each arm 8a, 8b may be oriented as preferred in any direction, as illustrated by the arrows in FIG. 2, by rotating it about a perpendicular axis to the substantially horizontal plane containing the frame 2 and/or by rotating it about a longitudinal axis passing through the maxillary crossmembers 5a, 5b.

Through the adjustments described above, it is easily and quickly possible to adapt the gag to the particular shape of the upper dental arch of the patient and to ensure that during use of the mouth gag each arm 8a, 8b rests on the upper premolars/molars in a substantially parallel direction thereto (i.e. a longitudinal direction to the upper molars). Once the desired adjustments have been performed, the gag is locked in such a position through the various clamping elements 12.

In order to have a better longitudinal support on the upper premolars/molars, passing over the incisors or the canines, each element 8a, 8b comprises a curved area 9a, 9b.

FIGS. 5, 6, 7 and 8 show an arm 8b resting on the upper premolars/molars when the gag is in use, i.e. resting on the face of the patient.

Advantageously, adjustment means 41a, 41b are provided on the uprights 4a, 4b that allow the length of each upright 4a, 4b to be extended or shortened and/or each upright 4a, 4b to be rotated with respect to the longitudinal axis passing through the upright itself.

Preferably, the frame 2 comprises adjustment means 6a, 6b for adjusting the length of the maxillary crossmember 5a, 5b that allow the rotation of the elements 8a, 8b on a sagittal plane.

All the adjustments described above allow great flexibility in the use of the mouth gag, allowing it to be adapted to the particular shape of the oral cavity of the patient.

The frame 2 further comprises at the bottom a housing 10, present in the maxillary crossmember 3 adapted to slidably receive the grip 23 of a tongue depressor blade inside it.

The mouth gag 1 also comprises a tongue depressor blade 21, 30 that is insertable in the oral cavity of the patient and that is movable with respect to the frame 2.

The tongue depressor blade comprises a tongue spatula 21, substantially perpendicular to the frontal or coronal plane (when inserted in use in the mouth gag), configured to depress and press the patient's tongue against the mandibular floor; and a substantially spoon-shaped element 30 that is longitudinally slidable with respect to the tongue spatula 21 so as to extend or shorten the total length of the tongue depressor blade 21, 30. The tongue spatula 21 comprises a lateral beveling 29 adapted to facilitate the insertion and extraction thereof from the oral cavity. Furthermore, the tongue spatula 21 comprises a grip 23, substantially perpendicular to the spatula 21, which is slidable in the vertical housing 10 of the mouth gag.

The grip 23 terminates with a curved end 25 and comprises a rack 24, e.g. comprising oblique teeth, engageable with a release and stop element 12 of the housing 10. By keeping the release element 12 pressed, it is possible to make the grip 23 slide upwards or downwards and, therefore, the tongue spatula 21 so as to be able to adjust the position thereof with respect to the patient's tongue. Once the desired vertical position has been found, e.g. with the spatula 21 pressing the tongue against the mandibular floor, the position of the spatula 21 is locked, releasing the release element 12.

Figure 14:
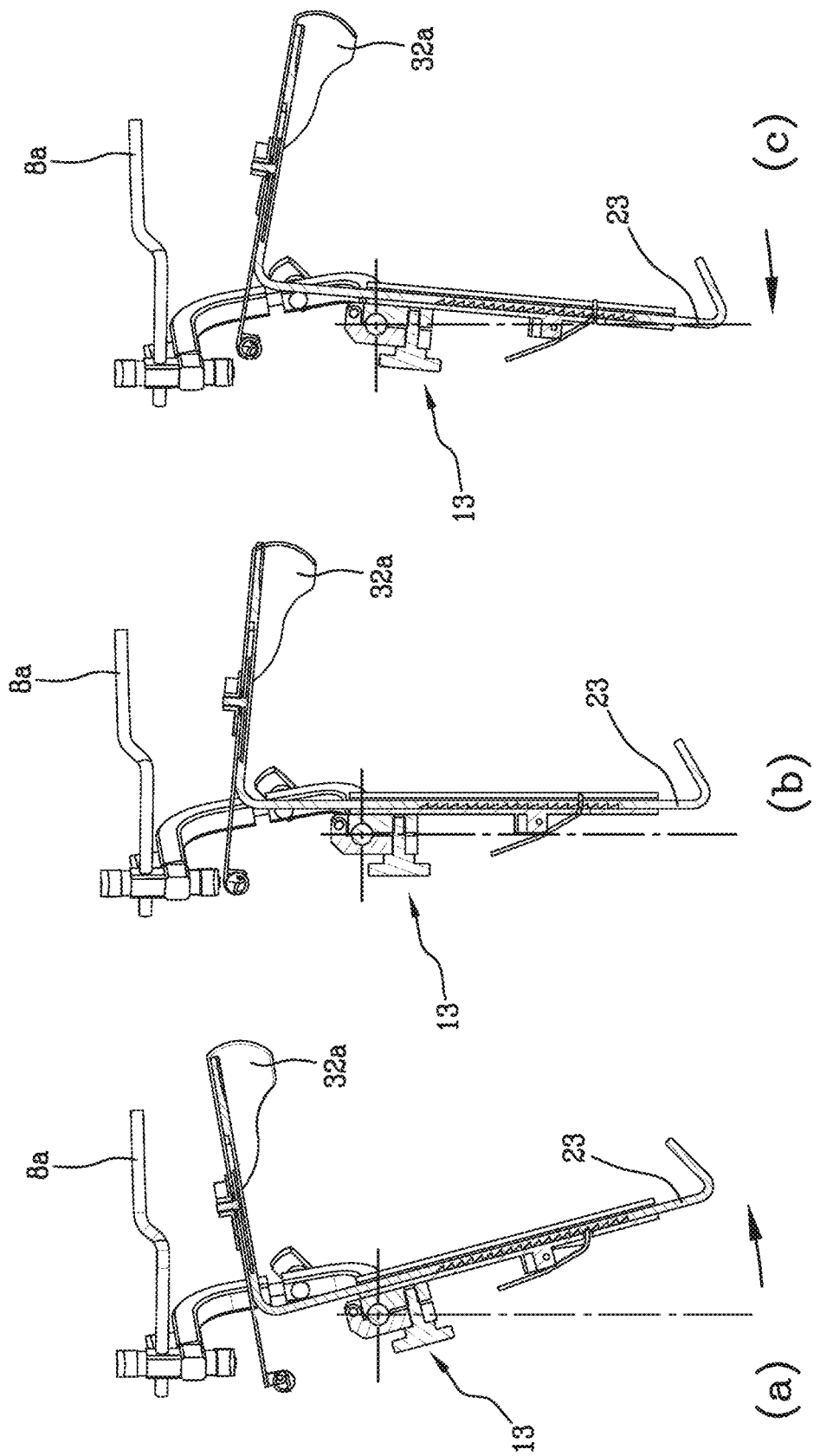
FIG. 14 shows a lateral sectional view of the mouth gag that illustrates three different angles assumed by the tongue depressor blade with respect to the frame.
Figure 15:
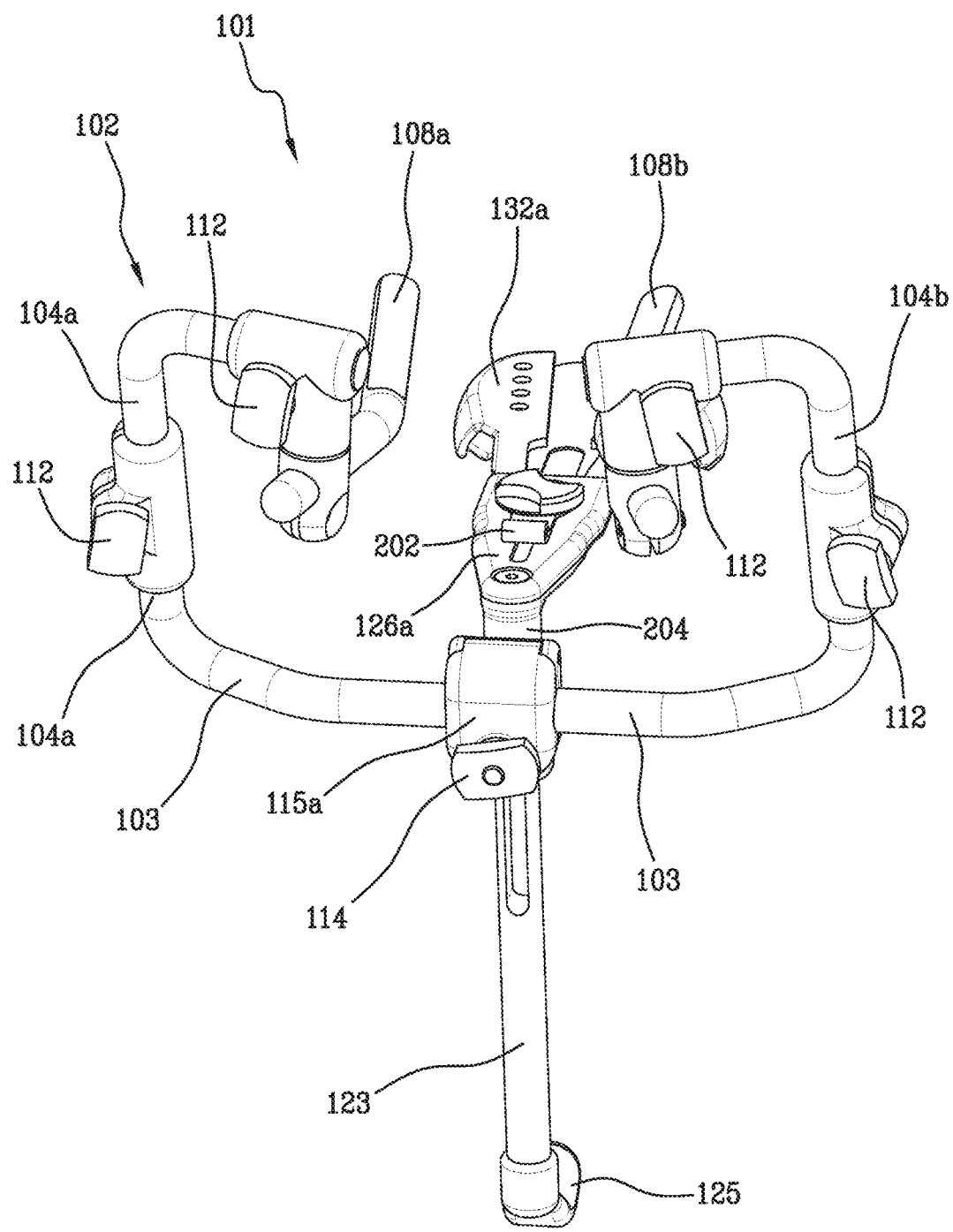
FIG. 15 shows a rear perspective view of a second embodiment of a surgical mouth gag according to the invention.
Figure 16:
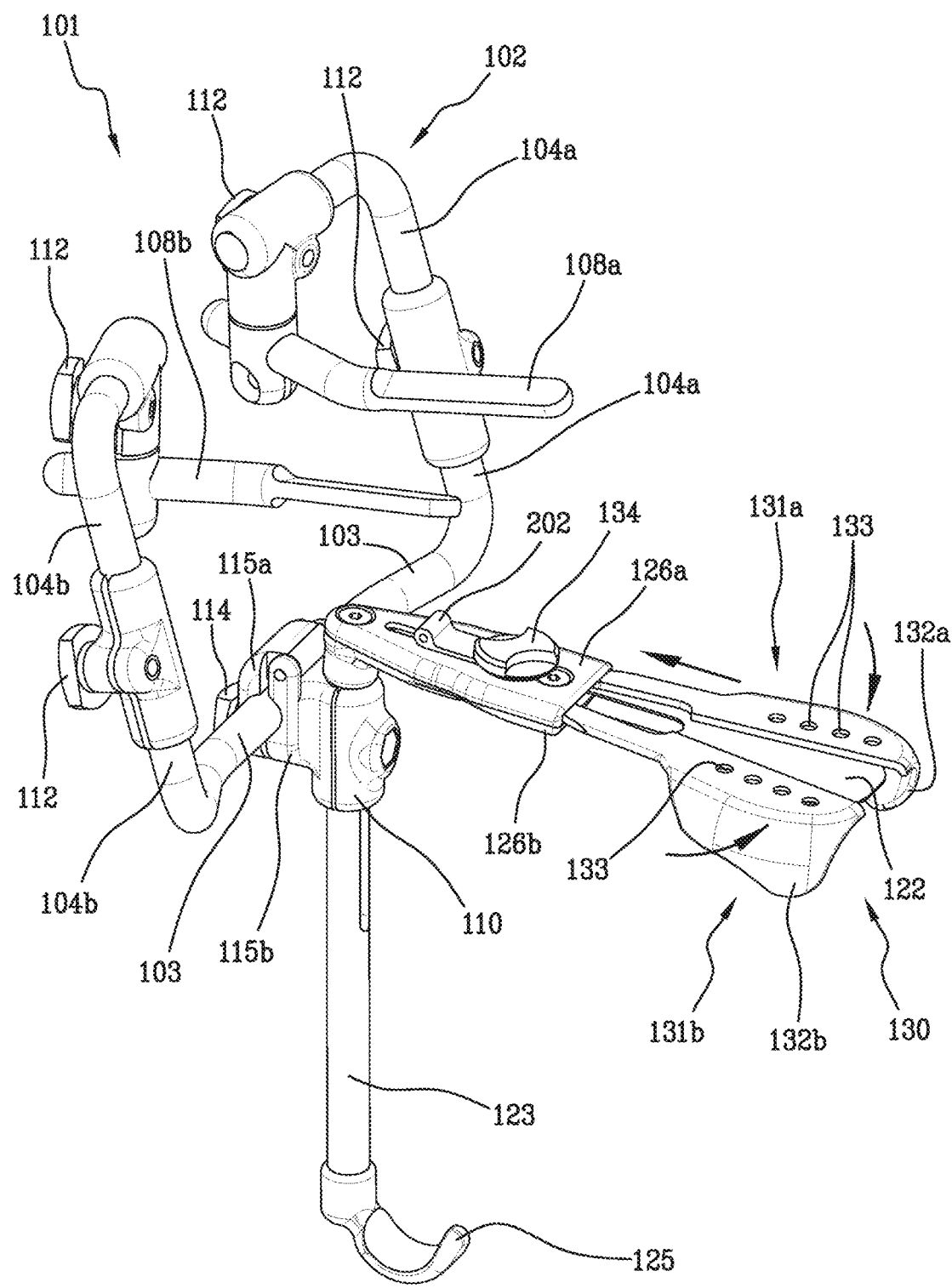
FIG. 16 shows the surgical mouth gag of FIG. 15 in a front lateral perspective view.
Figure 18:
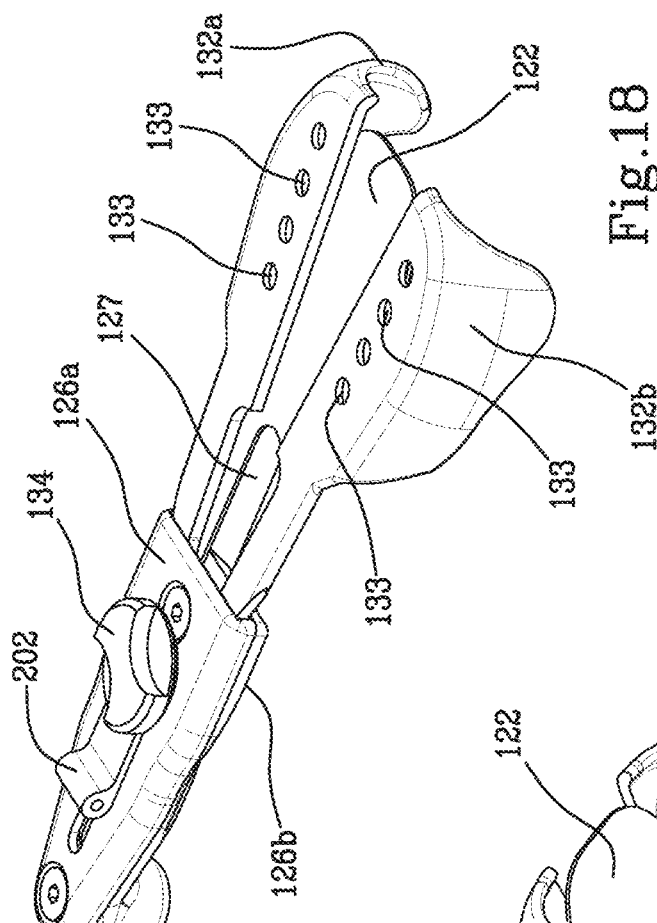
FIGS. 17 and 18 show the tongue depressor blade of FIGS. 15 and 16, in views from below and from above, respectively.
Figure 17:
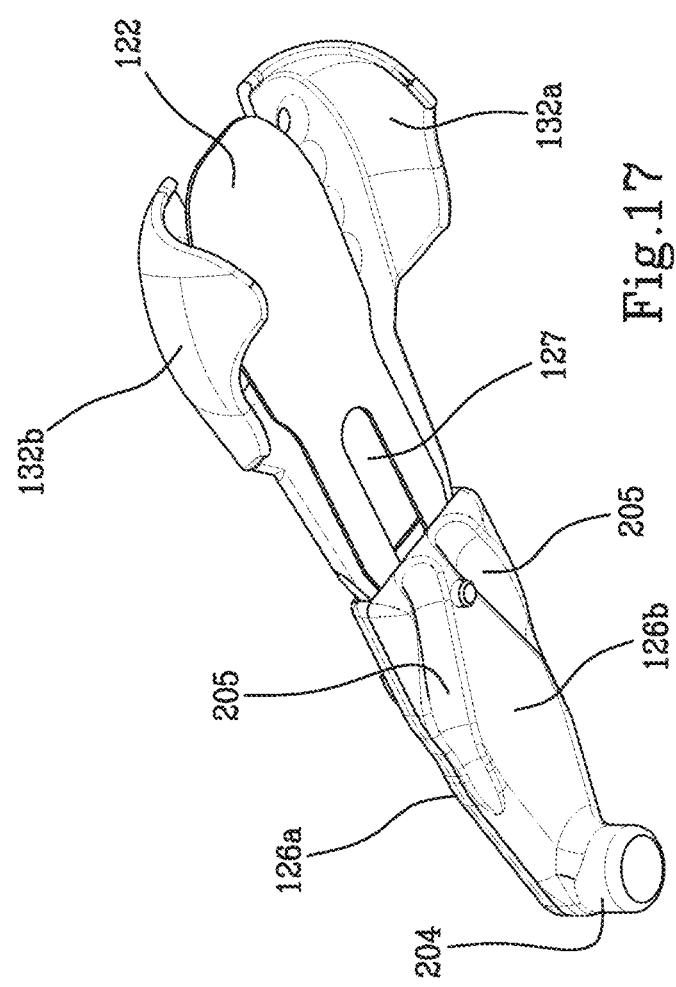

As illustrated in the sequence of FIG. 14, the tongue spatula 21 is rotatable in a superior/inferior direction with respect to the frame 2 (on the median sagittal plane) so as to be able to regulate the direction of the downward push on the anterior part of the tongue.

According to a non-limiting example of the present invention, the adjustment of the rotation of the tongue spatula 21 with respect to the frame 2 takes place by acting on a locking-unlocking element 14 that acts in turn on a clamping vice 13 comprising two jaws 15a, 15b. Each of the two jaws 15a, 15b has a complementary groove or seat 16a, 16b able to house inside it a cylindrical portion 20 of the mandibular crossmember 3. One of the two jaws 15a, 15b is solidly constrained to the housing 10 (e.g. welded thereto) and the two jaws 15a, 15b are hinged to each other around and joined by a pin 17.

The adjustment of the angle of the tongue depressor blade 21 with respect to the frame 2 takes place by unlocking the clamping element 14 which, by loosening the pressure of the jaws 15a, 15b on the cylindrical portion 20, allows the tongue depressor blade 21 to be rotated with respect to the frame as preferred and fixed in the correct position. By tightening the clamping element 14 again, the two jaws 15a, 15b act by tightening the vice 13 on the cylindrical portion 20 of the frame, blocking its possibility to rotate.

Preferably, the cylindrical portion 20 has a smaller diameter than the rest of the mandibular crossmember 3 and can comprise a striped "ribbed" type surface (substantially extending along a parallel direction to the longitudinal direction of the mandibular crossmember 3) so as to increase the friction and grip with the corresponding longitudinal seats 16a, 16b of the vice 13.

Figure 3:
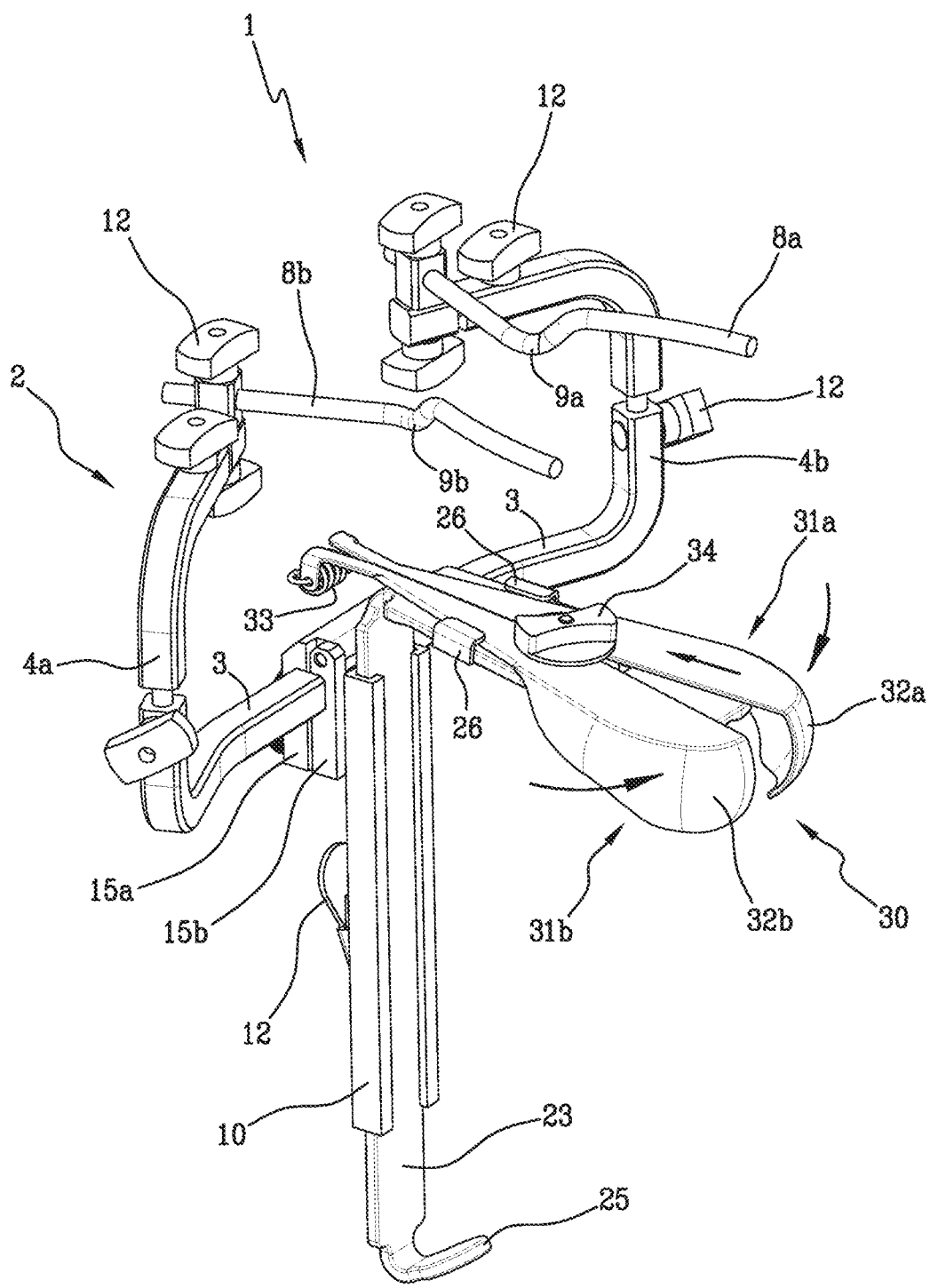
FIG. 3 shows the surgical mouth gag of FIG. 2 in a front lateral perspective view.
Figure 4:
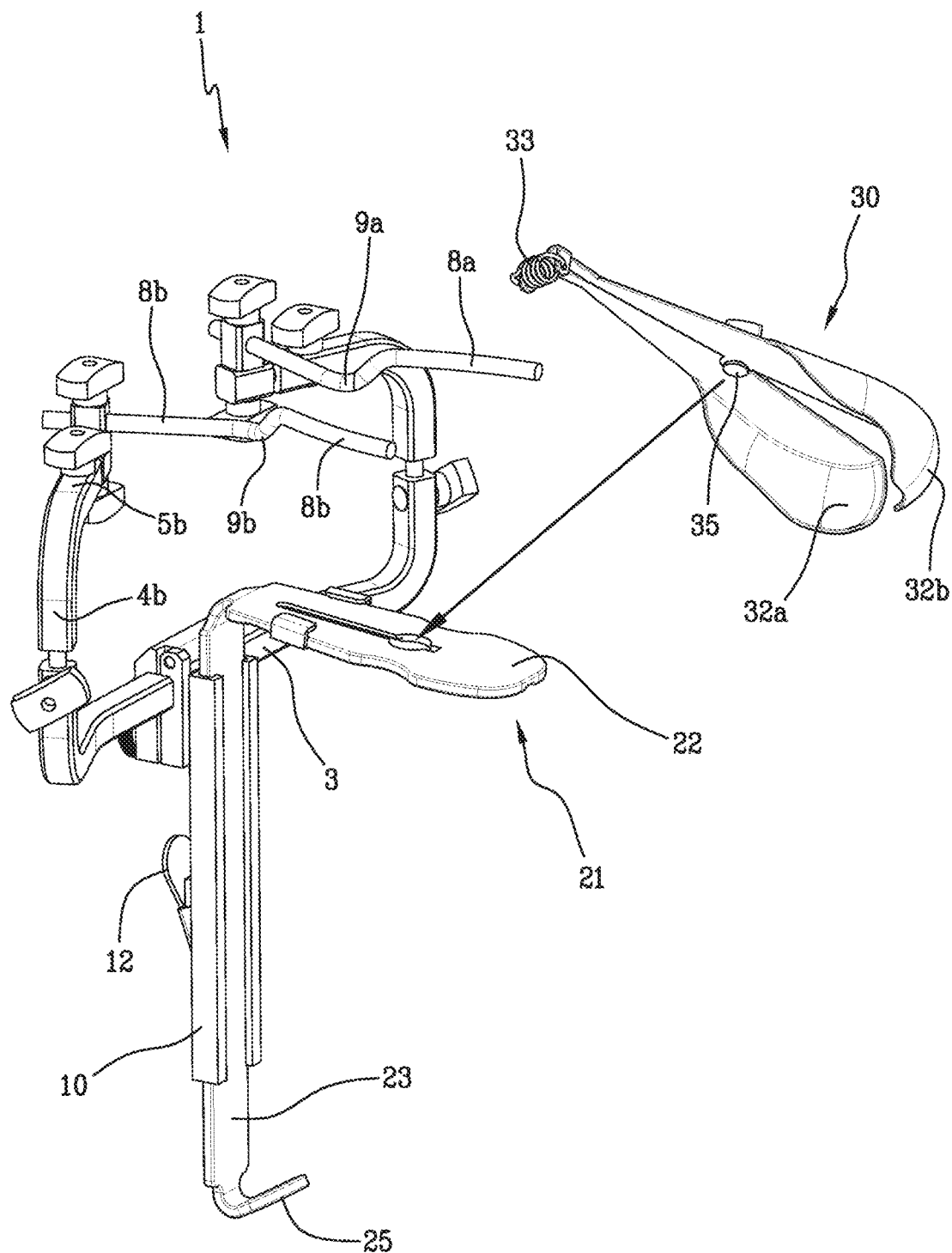
FIG. 4 shows a detail of the mouth gag of FIG. 3.
Figure 5:
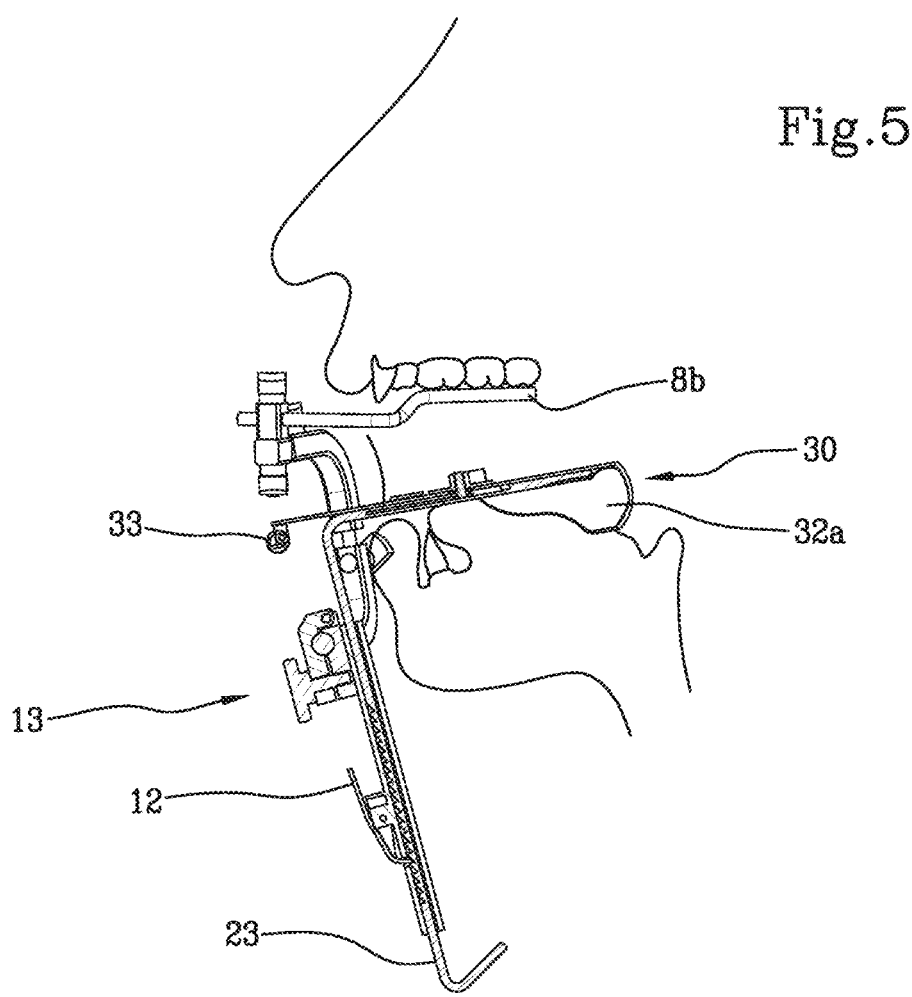
FIG. 5 shows a lateral section of the mouth gag with the tongue depressor blade inserted in the oral cavity and pressed against the tongue.
Figure 6:
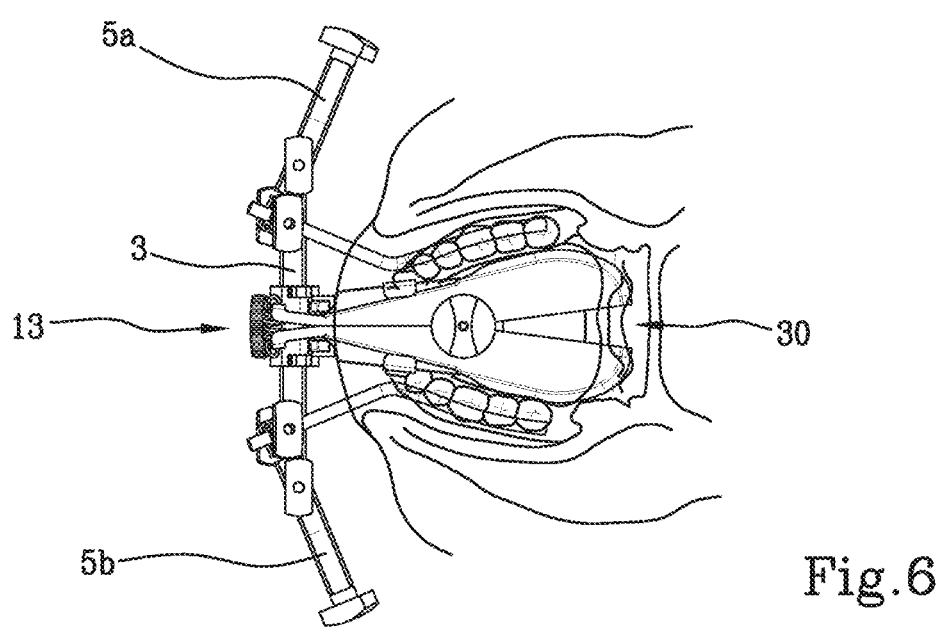
FIG. 6 shows the mouth gag of FIG. 5 in a view from above.
Figure 7:
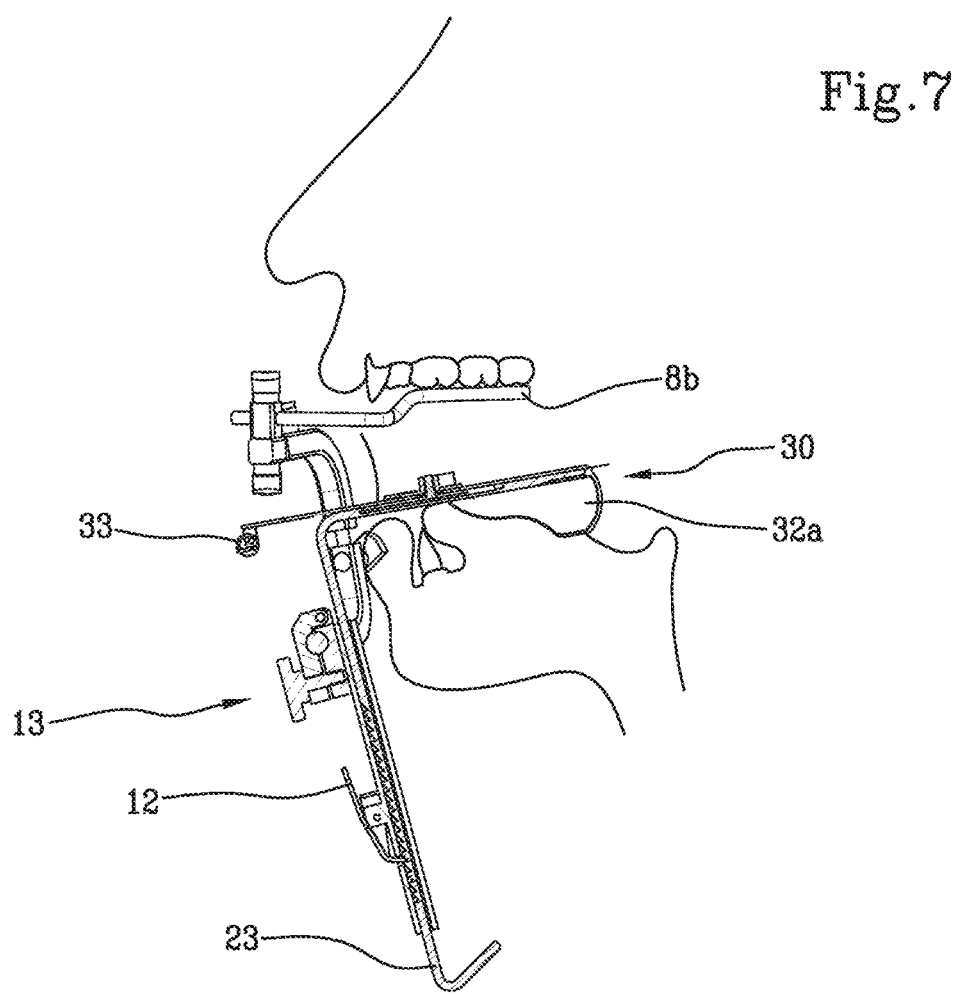
FIG. 7 shows the mouth gag of FIG. 5 with the tongue depressor blade made to slide towards the outside of the oral cavity.
Figure 8:
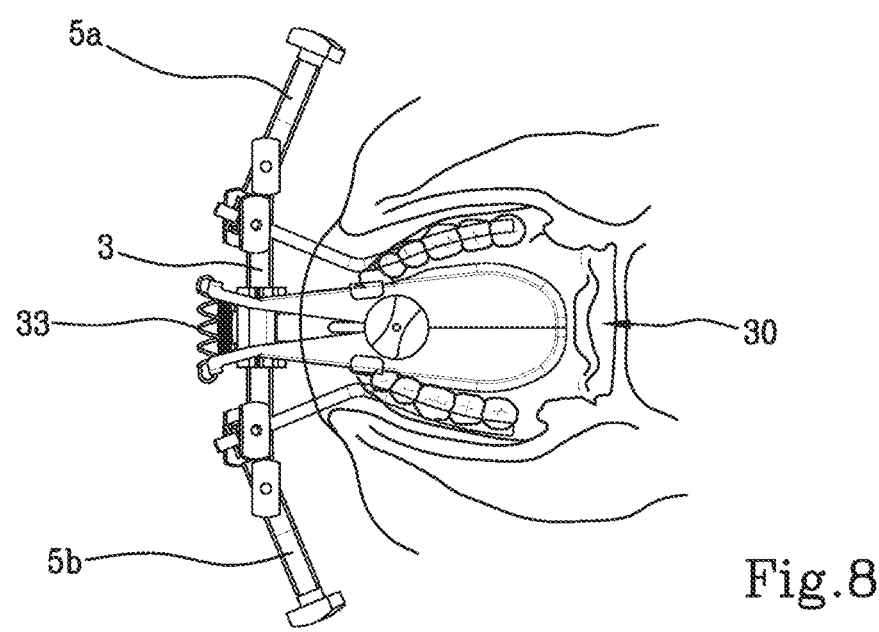
FIG. 8 shows the mouth gag of FIG. 7 in a view from above.
Figure 9:
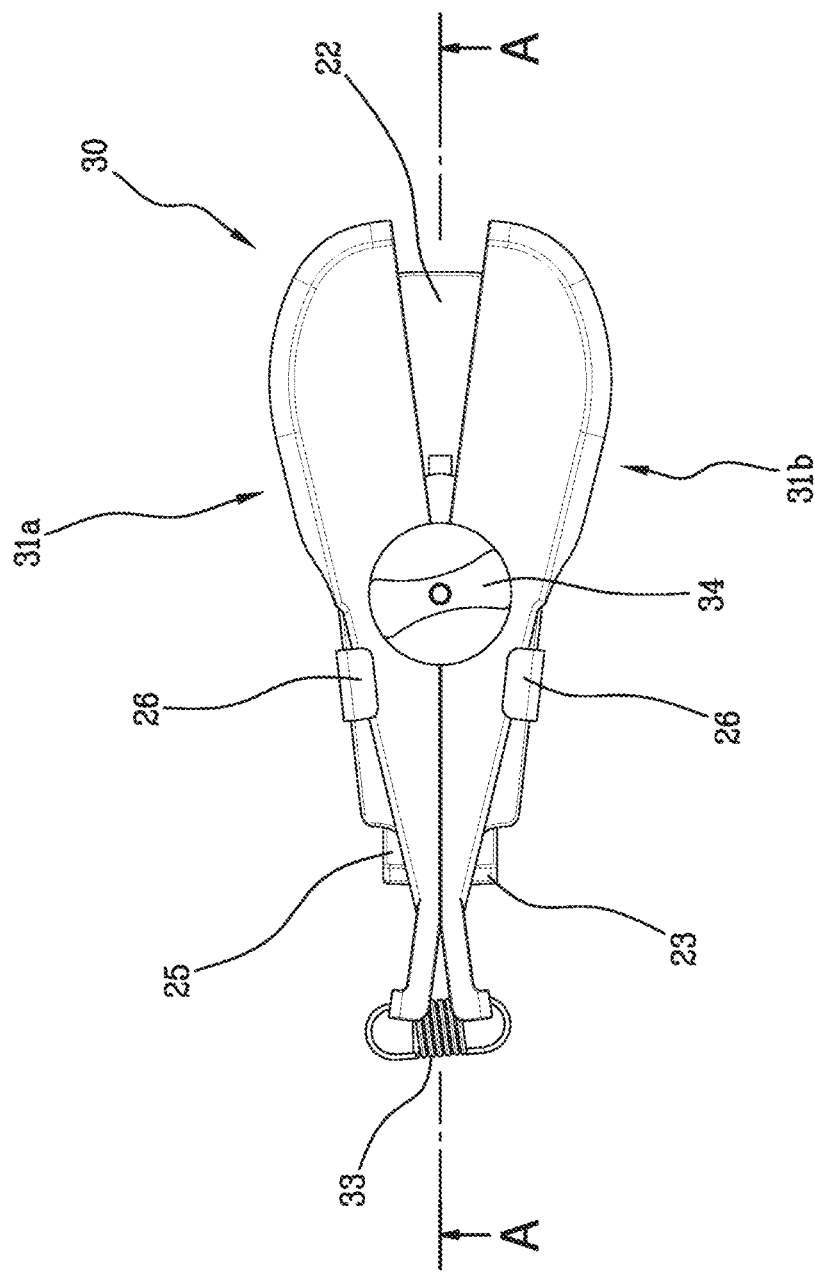
FIG. 9 shows a tongue depressor blade according to the present invention.
Figure 10:
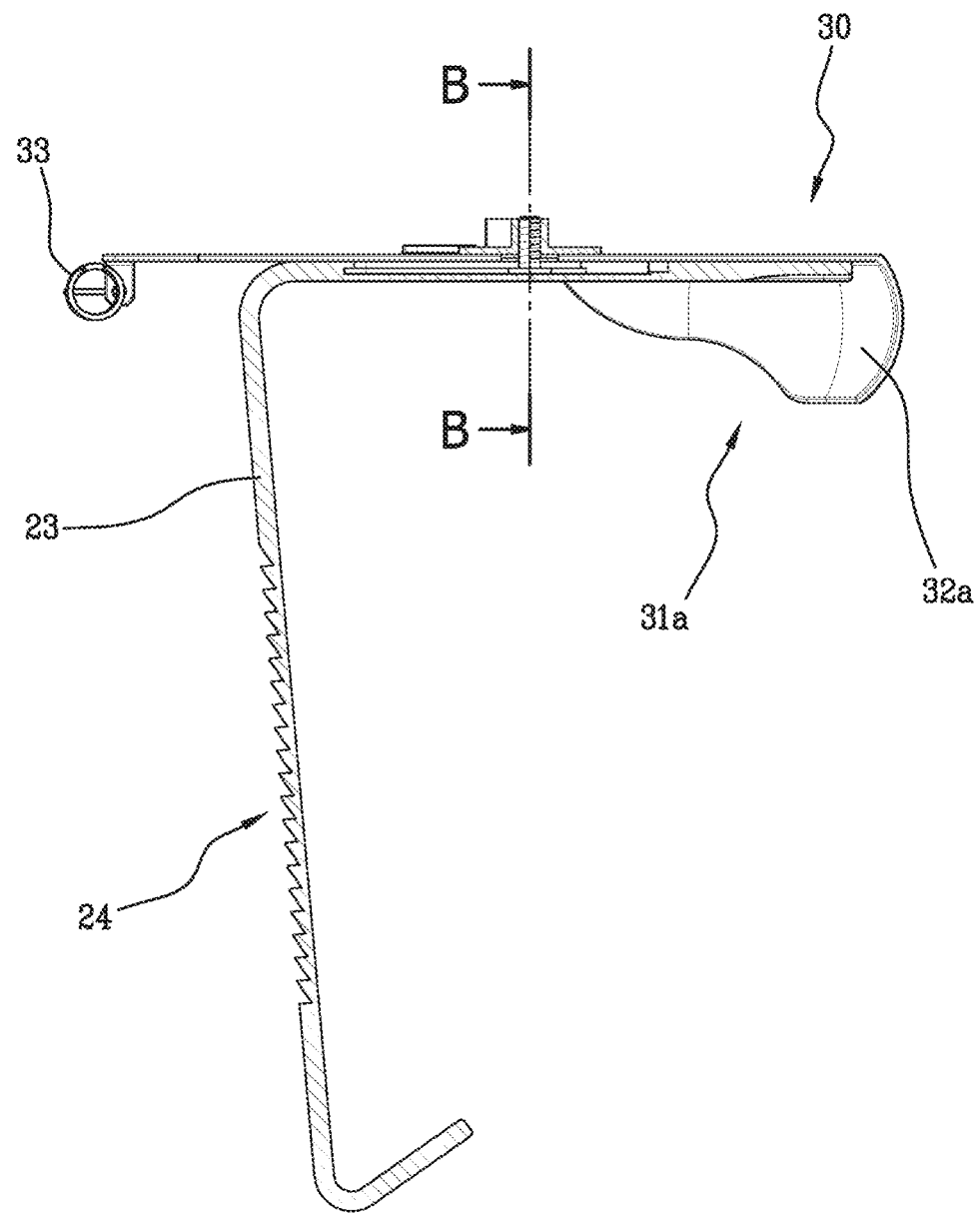
FIG. 10 shows a lateral view of the section A-A of the tongue depressor blade of FIG. 9.
Figure 11:
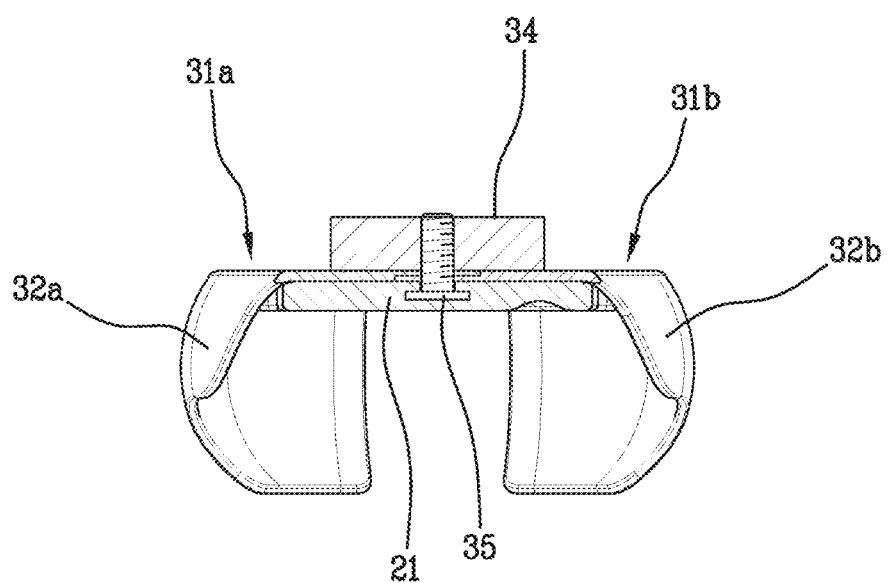
FIG. 11 shows a rear view of the section B-B of the tongue depressor blade of FIG. 10.
Figure 12:
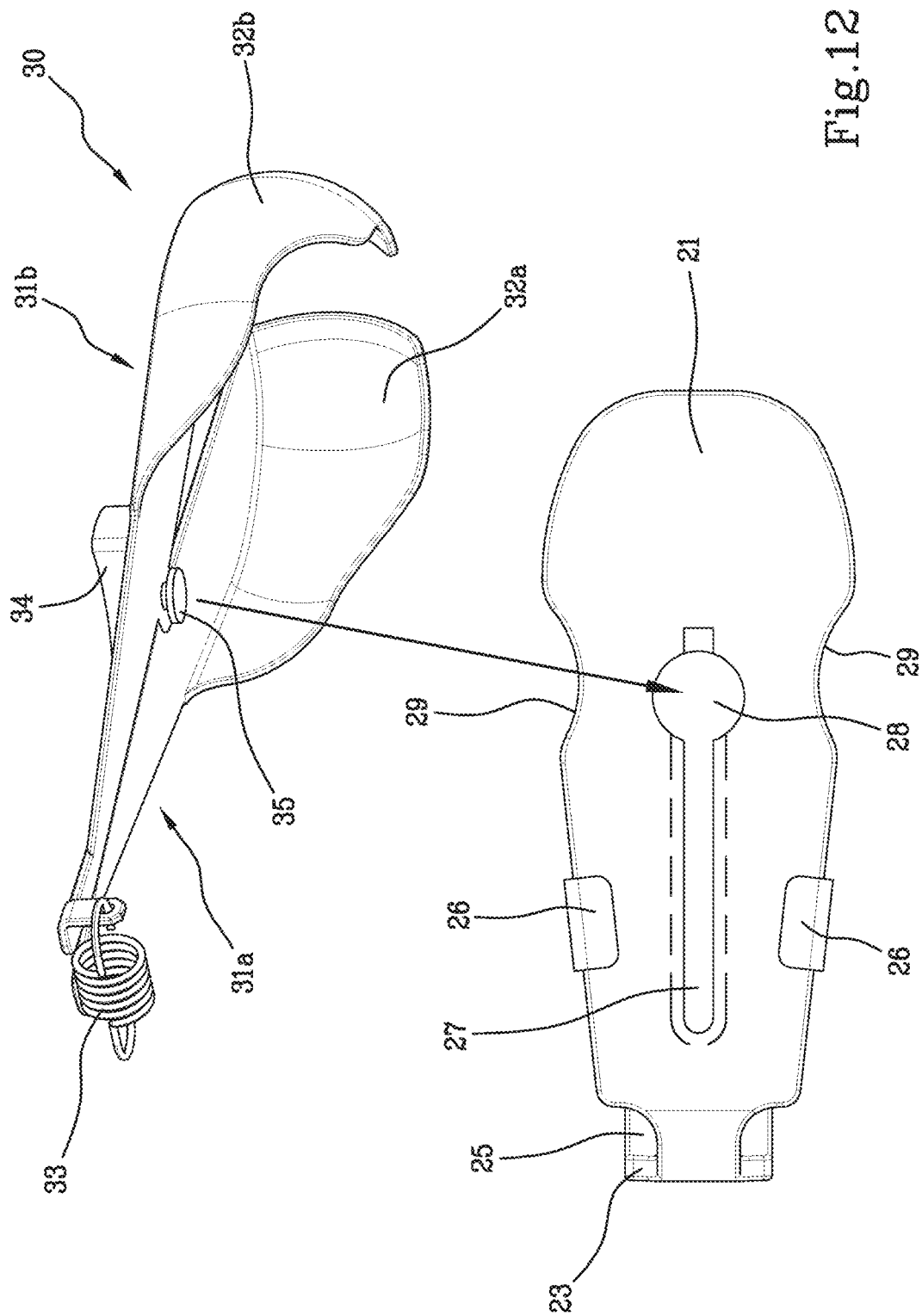
FIG. 12 shows a detail related to the coupling of two elements of the tongue depressor blade.
Figure 13:
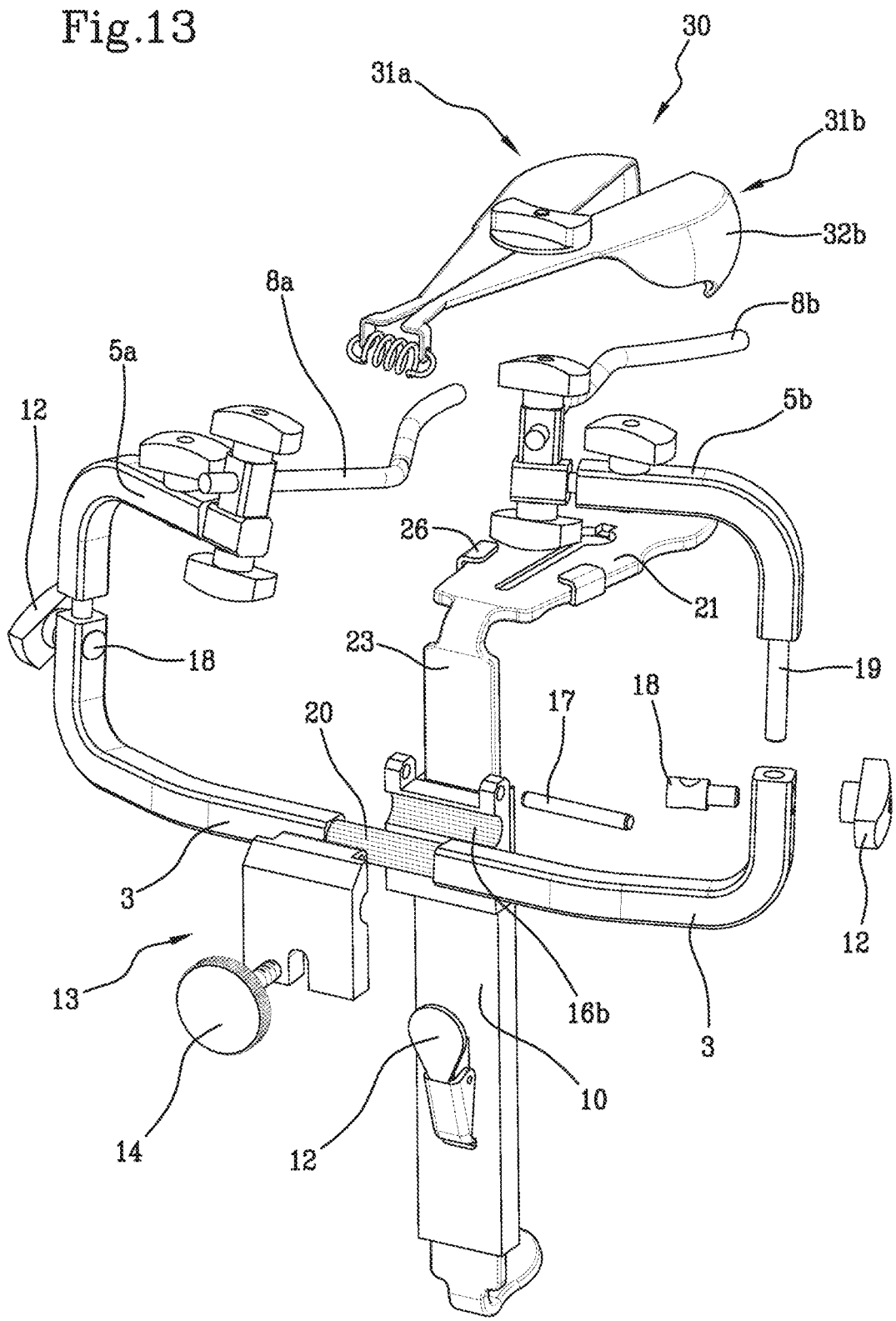
FIG. 13 shows a partially exploded view of a surgical mouth gag according to the invention.

The spoon-shaped element 30 comprises two elements 31a, 31b, with a substantially elongated shape, alongside each other, parallel to the tongue spatula 21 and able to rotate about a pin 35 as shown in FIG. 3.

The two elements 31a, 31b have at the front (end insertable inside the oral cavity) the shape of two half-spoons 32a, 32b with concavity facing downwards, able to entirely house the lingual base. The two rear ends of the two elements 31a, 31b form a rear grip (external end to the oral cavity when the gag is in use). When the two half-spoons 32a, 32b are in contact with each other, the two rear ends are slightly splayed out from each other. An elastic traction element 33 (e.g. a traction spring) keeps the two rear grips together so that the two half-spoons 32a, 32b are distanced from the mutual contact position resulting in a maximum width dimension configuration (meaning the distance from cheek to cheek) such as to allow the base of the tongue to be completely captured.

The tongue spatula 21 comprises a movable coupling means to the spoon shaped element 30. In particular, the tongue spatula 21 comprises a central longitudinal groove 27 inside which the pin 35 of the half-spoons 32a, 32b can slide so as to be able to extend or shorten the total length of the tongue depressor blade 21, 30.

The longitudinal groove 27 comprises a hole 28 adapted to allow the coupling with the pin 35 of the half-spoons 32a, 32b.

The tongue spatula 21 comprises two opposite lateral guides 26, in the half comprised between the two rear grips and the hole 28, adapted to make the two elongate elements 31a, 31b slide so that when the elements 31a, 31b are retracted (and therefore the total length of the tongue depressor blade in the oral cavity is shortened) the two half-spoons 32a, 32b tend to move closer together and towards the centre of the longitudinal axis of the tongue depressor spatula 21, thus gradually reducing the total width of the tongue depressor blade 21, 30.

The reduction in the width of the tongue depressor blade allows it to pass between the lower molars and any insertion or extraction of the gag from the oral cavity.

Vice versa, by pushing the rear grips of the elongate elements 31a, 31b longitudinally towards the oral cavity, the length of the tongue depressor blade 21, 30 is increased and the joint action of the lateral guides 26, spring 33 and pin 35 allows the two half-spoons 32a, 32b to be distanced from each other from the centre of the longitudinal axis of the tongue depressor spatula 21, so as to increase the width of the tongue depressor blade. Such increase in width allows the whole lingual base to be collected and contained.

The two half-spoons 31a, 31b further comprise a fixing element 34 that allows the width to be fixed and the possibility of the tongue depressor blade to slide longitudinally, fixing the two elongate elements 31a, 31b onto the tongue spatula 21.

In an alternative embodiment of the invention, the guides 26 of the tongue spatula 21 are configured to be coupled in a rack-like way with the outer lateral edges of the elongate elements 31a, 31b.

Once the tongue depressor blade 21, 30 has been inserted inside the oral cavity and passed between the lower molars, the increased width of the tongue depressor blade and any rotation in the upper-lower direction with respect to the frame 2 allow the tongue base region to be completely embraced and the downward push direction on the anterior part of the tongue to be modulated. Such operation allows the hard palate-soft palate junction to be suitably exposed and the glossotonsillar sulcus to be suitably exposed.

The gag 1 described above is essentially comprised of two elements: a frame 2 that keeps the patient's mouth as open as possible and supports a tongue depressor blade in the pressed position on the tongue.

However, it is observed that having a gag as described above with a tongue depressor blade of the known type constitutes an invention in itself. This gag solves the technical problem of reducing the risk of dental lesions, in particular of the upper incisors, during attempts to obtain more suitable exposure of the oropharyngeal organs.

Furthermore, it allows great flexibility in the use of the gag, allowing a single instrument to be adapted to the particular shape of the oral cavity of the patient.

In this case, the surgical mouth gag comprises a frame 2 adapted to be arranged in use around the mouth of the patient and having a larger size than the maximum aperture of the mouth, the frame 2 comprising a mandibular crossmember 3, at least one maxillary crossmember 5a, 5b, two uprights 4a, 4b that connect the mandibular crossmember 3 to the maxillary crossmember 5a, 5b, two upper arms 8a, 8b adapted to rest longitudinally on the upper premolars/molars when in use. The frame 2 can further comprise a housing 10, e.g. present on the maxillary crossmember 3 adapted to slidably receive the grip of a tongue depressor blade of the known type inside it.

It constitutes another invention in itself having a tongue depressor blade 21, 30 as described above, whose grip 23 can be installed in a housing of a perioral supporting arch or frame of the known type.

This tongue depressor blade, comprised of two elements, solves the technical problem of suitably exposing the hard palate-soft palate junction and suitably and bilaterally exposing the glossotonsillar sulcus.

It further allows the lingual base to advance fully to the glossotonsillar sulci positioning the tongue depressor blade in the space that separates the lower molars, normally smaller than the width of the lingual base.

In this case, the tongue depressor blade 21, 30 for the surgical mouth gag of the known type is insertable in the oral cavity of the patient and movable with respect to the frame of the mouth gag. The tongue depressor blade 21, 30 comprises a tongue spatula 21 perpendicular to the frontal/coronal plane and is configured to depress the patient's tongue against the mandibular floor; a spoon-shaped element 30 that is longitudinally slidable with respect to the tongue spatula 21 so as to extend the total length of the tongue depressor blade 21, 30.

The spoon-shaped element 30 comprises at the front two transversally movable half-spoons 31a, 31b so as to be able to vary the width of the tongue depressor blade 21, 30 from a minimum width such as to allow the tongue depressor blade 21, 30 to pass between the lower molars to a maximum width such as to allow the entire tongue base region to be fully embraced.

As described above, the improved surgical mouth gag according to the present invention comprises: a) an advantageous tongue depressor system (comprising two blades articulated to each other able to mobilise in a graduated way the entire tongue base both in the caudal and posterior-anterior direction); b) a metal arch, which supports and anchors the aforesaid tongue depressor system, characterised by resting on the upper premolar and molar teeth (respecting the incisors) and acts as an anterior window adapted to guarantee both the optimal exposure of the palatal structures and of the isthmus of the fauces and to facilitate the performance of palatal and oropharyngeal surgery in general and that of obstructive sleep disorders in particular.

FIGS. 15 to 19 represent a second embodiment of the surgical mouth gag previously described with reference to FIGS. 1-14. Below is a description of the differences only with respect to the description of the first embodiment, while for the analogous technical features reference is to be made to the description of the first embodiment. Furthermore, in FIGS. 15 to 18, analogous elements have been indicated with the prefix "10".

The surgical mouth gag 101, comprises a frame 102 (comprising a mandibular crossmember 103, a maxillary crossmember 105a,105b, two uprights 104a, 104b), two upper arms or vanes 108a,108b adapted to rest on the patient's upper molars, when in use. Preferably, the frame of the mouth gag 101 is round. The upper vanes 108a,108b preferably have an end with a flat shape so as to facilitate the insertion and extraction of a soft disposable sheath (for hygiene reasons), configured not to ruin the upper molars on which each vane 108a, 108b rests.

In the second embodiment, the grip 123 comprises a tubular element that terminates in the lower end with a hook 125 and that is slidable inside a double locking element 110 that also acts partially as a housing. There is also a complementary double locking element 115a able to house inside it a portion of the mandibular crossmember 103. The inclination of the tongue depressor assembly can be adjusted using the central knob 114. In the second embodiment, the tongue depressor blade comprises a tongue spatula 122 and a spoon-shaped element 130 longitudinally slidable with respect to the tongue spatula 122, comprising two elongate elements 132a, 132b. Preferably, each of the two elongate elements 132a, 132b comprises one or more through holes 133 that allow the physician to be able to check the colour of the patient's tongue when the tongue depressor blade is kept pressed on the tongue. In this way, it can be verified whether the patient's tongue is being pressed too much during the mouth gag operation. Alternatively, the spoon-shaped element could be made of transparent material. Preferably, the tongue spatula 122 is made of Teflon.

The tongue spatula 122 and the two elongated spoon-shaped elements 132a, 132b comprise at one end a through hole 200 through which a pin passes which keeps them hinged at the grip 123 and they are comprised inside two half-shells 126a, 126b. The upper half-shell or cover 126a comprises a longitudinal through groove 127a and a second through hole 201, while the lower half-shell or tongue depressor base 126b comprises a longitudinal groove 127b, at the groove of the first half-shell 126a, in which a nut 203 can slide longitudinally. On one end of the lower half-shell 126b there is a housing 204 for the upper part of the grip 123. There is also a fixing element 134 that allows the tongue depressor blade 122, 132a, 132b to slide longitudinally and/or to fix the two elongate elements 132a, 132b to the tongue spatula 122 in the desired position, acting on a knob element for forceps or tabs 202. The particular shape of the two half-shells 126a, 126b allows, while advancing and/or retracting the spoon-shaped element 130 the two elongate elements 132a, 132b to be splayed apart or moved closer together. Preferably, the width of the free end of the tongue depressor blade 122 must be such as to at least cover the space present between the two elongated spoon-shaped elements 132a, 132b when they are splayed apart at the maximum distance from each other. This prevents any "pinching" of the patient's tongue when the two elongated spoon-shaped elements 132a, 132b have collected the base of the tongue and are moved closer together. It is to be noted that, in another non-limiting example of the present invention, the mouth gag described above can be easily applied to the oral cavity of an animal.

The invention claimed is:

1. A mouth gag for exposing the palatal and oropharyngeal region of a patient, comprising:
   a frame suitable for being arranged in use around the mouth of the patient and being of a size that is larger than the maximum aperture of the mouth, the frame comprising:
      a mandibular crossmember,
      a maxillary crossmember,
      two uprights that connect the mandibular crossmember to the maxillary crossmember,
      an upper arm that is suitable for resting on the upper molars when in use;
   a tongue depressor blade that is insertable in the oral cavity of the patient and that is movable with respect to the frame, the tongue depressor blade comprising:
      a tongue spatula configured to depress the patient's tongue against the mandibular floor;
      a spoon-shaped element that is longitudinally slidable with respect to the tongue spatula so as to extend the length of the tongue depressor blade,
   the spoon-shaped element being constituted by two elongate elements that are movable so as to vary the width of the tongue depressor blade from a minimum width, which is such as to enable passage of the tongue depressor blade between the lower molars, to a maximum width, which is such as to enable them to embrace the entire tongue base region,
   wherein the two elongate elements are hinged to a pin so as to enable transverse movement in the transverse plane.

2. The mouth gag according to claim 1, comprising two maxillary crossmembers and two upper arms, each arm being movably connected to one of the two maxillary crossmembers.

3. The mouth gag according to claim 2, wherein the frame comprises adjustment means for adjusting the two upper arms, said means being such as to allow the two upper arms to rotate about the longitudinal axis of the respective maxillary crossmember and/or to change the length thereof.

4. The mouth gag according to claim 1, wherein the frame comprises adjustment means for adjusting the length of the maxillary crossmember.

5. The mouth gag according to claim 1, wherein the frame comprises adjustment means for adjusting the length and the rotation of the two uprights with respect to the longitudinal axis of the two uprights.

6. The mouth gag according to claim 1, wherein the tongue spatula proves to be rotatable in a superior/inferior direction with respect to the frame so as to make it possible to regulate the direction of the downward push on the anterior part of the tongue.

7. The mouth gag according to claim 1, wherein each arm has a curved area suitable for passing over the canines and for ensuring that the end of each arm rests laterally on the upper premolars and molars.

8. The mouth gag according to claim 1, wherein the tongue spatula comprises movable coupling means for coupling with the spoon-shaped element.

9. The mouth gag according to claim 1, wherein the tongue spatula comprises a longitudinal groove within which the pin can slide.

10. The mouth gag according to claim 9, wherein the longitudinal groove comprises a hole suitable for enabling coupling with the pin.

11. The mouth gag according to claim 1, wherein the tongue spatula comprises two lateral guides suitable for sliding the two elongate elements longitudinally.

12. The mouth gag according to claim 1, wherein the tongue spatula comprises a grip that is substantially perpendicular to the spatula and the grip proves to be slidable in a housing fixed on the mandibular crossmember.

13. The mouth gag according to claim 1, wherein the housing comprises a stop element that acts upon a rack of the grip in such a manner that the tongue depressor spatula can be adjusted/stopped in various positions.

14. A mouth gag for exposing the palatal and oropharyngeal region of a patient, comprising:
   a frame suitable for being arranged in use around the mouth of the patient and being of a size that is larger than the maximum aperture of the mouth, the frame comprising:
      a mandibular crossmember,
      a maxillary crossmember,
      two uprights that connect the mandibular crossmember to the maxillary crossmember,
      an upper arm that is suitable for resting on the upper molars when in use;
   a tongue depressor blade that is insertable in the oral cavity of the patient and that is movable with respect to the frame, the tongue depressor blade comprising:
      a tongue spatula configured to depress the patient's tongue against the mandibular floor;
      a spoon-shaped element that is longitudinally slidable with respect to the tongue spatula so as to extend the length of the tongue depressor blade,
   the spoon-shaped element being constituted by two elongate elements that are movable so as to vary the width of the tongue depressor blade from a minimum width, which is such as to enable passage of the tongue depressor blade between the lower molars, to a maximum width, which is such as to enable them to embrace the entire tongue base region,
   wherein the two elongate elements comprise a spring at the end opposite the oral cavity and that is suitable for keeping them joined in a configuration of maximum aperture in width.

15. Method for exposing the palatal and oropharyngeal region of a patient, comprising the steps of:

providing a mouth gag comprising:
   a frame of a size that is larger than the maximum aperture of the mouth of the patient, the frame comprising:
      a mandibular crossmember,
      a maxillary crossmember,
      two uprights that connect the mandibular crossmember to the maxillary crossmember, and
      an upper arm;
   a tongue depressor blade comprising a tongue spatula;
   a spoon-shaped element that is longitudinally slidable with respect to the tongue spatula so as to extend the length of the tongue depressor blade,
   the spoon-shaped element being constituted by two elongate elements that are movable so as to vary the width of the tongue depressor blade from a minimum width, which is such as to enable passage of the tongue depressor blade between the lower molars, to a maximum width, which is such as to enable them to embrace the entire tongue base region,
   wherein the two elongate elements are hinged to a pin so as to enable transverse movement in the transverse plane;
arranging the frame of the mouth gag around the mouth of the patient;
resting the upper arm on the upper molars of the patient;
inserting the tongue depressor blade of the mouth gag in the oral cavity of the patient, and longitudinally moving the tongue depressor blade with respect to the frame;
increasing the width of the tongue depressor blade after the tongue depressor blade has passed between the lower molars;
depressing the patient's tongue against the oral floor with the tongue spatula of said tongue depressor blade, and simultaneously completely embracing the tongue base region with the spoon shaped element so as to expose the palatal and oropharyngeal region of the patient.

16. The method according to claim 15, further comprising adjusting the length of the maxillary crossmember with adjustment means of the frame.

17. The method according to claim 16, further comprising adjusting two upper arms, each arm being movably connected to one of the two maxillary crossmembers, by allowing the two upper arms to rotate about the longitudinal axis of the respective maxillary crossmember and/or to change the length thereof.

18. The method according to claim 16, further comprising adjusting the length and the rotation of the two uprights with respect to the longitudinal axis of the two uprights.

19. The method according to claim 15, further comprising regulating the direction of the downward push of the tongue spatula on the anterior part of the tongue, by rotating it in a superior/inferior direction with respect to the frame.

\* \* \* \* \*